United States Patent [19]

King et al.

[11] Patent Number: 4,497,719

[45] Date of Patent: Feb. 5, 1985

[54] METAL SALTS OF 1,2,4-THIADIAZOLE AND LUBRICANTS CONTAINING THESE METAL SALTS

[75] Inventors: James P. King, Lansdale; Paul Tubbs, Philadelphia, both of Pa.

[73] Assignee: Pennwalt Corporation, Philadelphia, Pa.

[21] Appl. No.: 426,526

[22] Filed: Sep. 29, 1982

[51] Int. Cl.³ .............................................. C10M 1/54
[52] U.S. Cl. .................................. 252/42.7; 252/28; 252/37; 252/42.1; 252/46.4; 548/105; 548/129
[58] Field of Search .................. 252/42.7, 46.4, 28, 252/37, 42.1; 548/105, 129

[56] References Cited

U.S. PATENT DOCUMENTS 2,285,410 6/1942 Bousquet et al. ............. 548/105 X
2,910,439 10/1959 Fields ............................ 252/42.7 X
3,634,442 1/1972 Seltzer ............................... 548/105
3,821,236 6/1974 Ripple ............................... 548/129

OTHER PUBLICATIONS

Indian J. of Chem., 1975, vol. 13(7), pp. 697–701.

*Primary Examiner*—Andrew Metz

[57] ABSTRACT

The metal salts of 1,2,4-thiadiazole having the structure

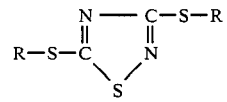

and lubricants containing said metal salts are provided.

4 Claims, No Drawings

METAL SALTS OF 1,2,4-THIADIAZOLE AND LUBRICANTS CONTAINING THESE METAL SALTS

BACKGROUND OF THE INVENTION

This invention relates to metal salts of 1,2,4-thiadiazole that are especially effective as additives in lubricants that enable the lubricants to withstand extremely high pressure and yet maintain antiwear properties. This invention also comprehends lubricant compositions containing the metal salts.

Copper and zinc salts of 2,5-dimercapto-1,3,4-thiadiazole for use as complexing agents were reported in the Indian Journal of Chemistry, 1975, Vol. 13 (7), at pages 697 to 701 (CA83; 107518r). U.S. Pat. No. 4,136,043 (Davis) teaches a composition prepared by reacting dimercaptothiadiazoles with an oil soluble dispersant which are used for suppression of copper activity and "lead paint" decomposition in lubricants. U.S. Pat. No. 4,183,816 discloses the use of 2,4-di(lower alkyl)-1,2,4-thiadiazolidin-3,5-diones as ashless load carrying additives for functional fluids. U.S. Pat. No. 4,188,299 teaches the additive prepared by reacting 2,5-dimercapto-1,3,4-thiadiazole thiophosphoric acid with an alkaline earth metal neutralization agent which additive is used as oil additives to enhance anticorrosion, antioxidant, and antiwear properties. U.S. Pat. Nos. 1,304,537, 3,821,236 and 3,904,619 disclose disulfides of 1,2,4-thiadiazoles. None of the above mentioned prior art teaches the instant invention.

Many lubricants which are satisfactory for ordinary lubricating applications do not provide adequate protection under extremely heavy load conditions, such as metal deformation, cutting and grinding, gear lubrication of heavy duty machinery, and bearing lubrication under severe conditions. Present lubricants made for these purposes include sulfurized and chlorinated hydrocarbon oils and oils containing such additives as molybdenum disulfide, tungsten sulfides, heavy metal salts of dialkyldithiocarbamic acids, heavy metal salts of dialkyldithiophosphoric acids, polymers of mercapto thiadiazoles and organic and inorganic lead compounds.

SUMMARY OF THE INVENTION

This invention is directed to:

A. A composition having the formula

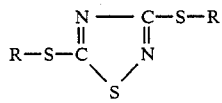

wherein R is a metallic ion.

B. A lubricating composition comprising a major amount of lubricating grease (or fluid) and a minor amount of the compound described in A, supra. The major amount is from about 80 to about 99.9 parts (percentage) of the lubricating grease and the minor amount is in the range from about 20 to about 0.1 parts, preferably 3 to 5 parts, of the metal salt of the 1,2,4-thiadiazole.

DETAILED DESCRIPTION OF THE INVENTION

The metal can be selected from various groups of the Periodic Table such as transition metals, coinage metals, zinc metals, etc. The elements—zinc, tin, cobalt, nickel, molybdenum, zirconium, silver, gold, platinum, and palladium are of particular interest.

The Shell Four-Ball Extreme Pressure (EP) Test was selected for evaluating the metal salts of the present invention. The Shell Four-Ball EP machine consists essentially of a chuck holding a ½-inch diameter steel ball and a cup holding three similar balls in contact. The chuck holding the one ball is rotated at constant speed for a period of 10 seconds, producing a wear scar on the three immobile balls, a constant load on the balls being applied by means of pivoted lever. At the end of the 10-second run the balls are removed and the mean wear scar diameter measured by means of a calibrated microscope. Initially, small increases in load produce small increases in the mean wear scar diameter; a point is reached, however, when a small increase in load produces a large increase in the mean wear scar diameter; this load is called the initial seizure load. Beyond this point, small increases in load again produce relatively small increases in the mean wear scar diameter until welding of the balls occur; this load is called the weld point. By obtaining 10 wear scar diameters under 10 different loads below the weld point, one can calculate the Load Wear Index (Mean-Hertz Load) which is a measure of the wear preventive ability of a lubricant at applied loads (I.P. Standards for Petroleum and Its Products, Method 239/73T; ASTM D-2596-69).

Four base greases, which represent a broad spectrum of the industrial greases used today, were selected to evaluate the new metal salts of the present invention as follows:

1. A lithium grease (mineral oil thickened with lithium 12-hydroxystearate).
2. A clay grease (mineral oil thickened with clay).
3. A silicone grease (silicone oil thickened with lithium stearate).
4. An aluminum complex grease (mineral oil thickened with aluminum complex soap). All of the base greases are products of the Keystone Division of the Pennwalt Corporation.

Liquid lubricants that are used in the lubricating compositions of the present invention are mineral oil, water, and synthetic fluids such as silicone fluid. It should be noted that other additives normally found in lubricating compositions can be included in the present lubricating composition such as antioxidants, corrosion inhibitors, detergents, suspension agents, viscosity index improvers, etc.

The following examples are provided to further illustrate the present invention; all parts (or percentages) are by weight unless otherwise stated.

EXAMPLE 1

Copper (II) 3,5-dimercapto-1,2,4-thiadiazole

A solution of 11.8 g (0.052 m) of dipotassium 3,5-dimercapto-1,2,4-thiadiazole in 140 ml water was slowly added with agitation to a solution of 8.9 g (0.052 m) of $CuCl_2 \cdot 2H_2O$ in 100 ml water. The resulting mixture was refluxed for 2.5 hours and a light green solid was isolated by means of filtration followed by several washings with distilled water and drying at 100° C. for 24 hours.

For the sake of comparison, the prior art metal salt of copper (II) 2,5-dimercapto-1,3,4-thiadiazole was prepared as follows. An aqueous solution of 10.1 g (0.052 m) disodium 2,5-dimercapto-1,3,4-thiadiazole in 25 ml water was added with agitation to a solution of 8.9 g (0.052 m) $CuCl_2.2H_2O$ in 60 ml water resulting in formation of reddish brown solid. The product was isolated by means of filtration followed by several washings with distilled water and drying at 75° C. for 24 hours.

The solid products of both the novel and prior art compounds were subjected to isothermal studies at 250° and 275° C. for 17 hours in air and the results were recorded in Table I. Evaluation results and elemental analysis of the solid products as an additive in a lithium grease are recorded in Table II.

TABLE I

| Isothermal Studies of Cu II $(1,2,4-C_2N_2S_3)$ and Cu II $(1,3,4-Cu_2N_2S_2)$* Wt. Loss (%) After Heating in Air for 17 hrs at | | |
|---|---|---|
| | 250° C. | 275° C. |
| Cu (II) $1,2,4-C_2N_2S_3$ | 13 | 25 |
| Cu (II) $1,3,4-C_2N_2S_3$ | 22 | 42 |
| *Elemental analyses of compounds: | | |
| Cu II $(1,2,4-C_2N_2S_3)$: | Found: | C, 11.4; N, 13.7; S, 43.7; Cu, 29.6 |
| | Calc.: | C, 11.3; N, 13.2; S, 45.4; Cu, 30.0 |
| Cu II $(1,3,4-C_2N_2S_3)$: | Found: | C, 11.2; N, 12.9; S, 41.9; Cu, 28.8 |
| | Calc.: | C, 11.3; N, 13.2; S, 45.4; Cu, 30.0 |

TABLE II

| Lubricating Properties of Cu II $(1,2,4-C_2N_2S_3)$ and Cu II $(1,3,4-C_2N_2S_3)$ in a Lithium Grease | | |
|---|---|---|
| | Lubricating Properties in Greases 1,2 | |
| | Weld Point, kg | Load Wear Index |
| Cu II $(1,2,4-C_2N_2S_3)$ | 400 | 80.9 |
| Cu II $(1,3,4-C_2N_2S_3)$ | 400 | 58.2 |

1 Lithium 12-OH stearate grease containing 5% additive.
2 ASTM D 2596 - AISI 52100 steel balls.

The long-term isothermal studies (Table I) of copper (II) 2,5-dimercapto-1,3,4-thiadiazole and copper (II) 3,5-dimercapto-1,2,4-thiadiazole show considerable difference in weight losses between these two isomers. The much higher percent weight loss of the copper (II) 2,5-dimercapto-1,3,4-thiadiazole at 275° C. than the 1,2,4-thiadiazole isomer will severely limit its potential for many applications. In addition, the Load-Wear Index of a lithium base grease containing 5% copper (II) 2,5-dimercapto-1,3,4-thiadiazole was much lower than that of the copper (II) 3,5-dimercapto-1,2,4-thiadiazole isomer as shown in Table II. The Load-Wear Index, which projects a complete profile of antiwear characteristics of a lubricant, is obtained by measuring Shell Four-Ball wear scar diameter with increasing load. The four-ball weld points of both greases containing these two additives were the same (400 kg); however, significant difference in wear scar diameters between 100 and 300 kg were also observed.

EXAMPLE 2

Zinc-3,5-dimercapto-1,2,4-thiadiazole

An aqueous solution of dipotassium 3,5-dimercapto-1,2,4-thiadiazole (5.0 g, 0.022 m) was added with agitation at room temperature to a solution of 5.0 g (0.022 m) of $Zn(OAc)_2.2H_2O$ in 60 ml of $H_2O$. A white solid formed immediately which was isolated by means of filtration. After it was washed several times with distilled water, the solid product was dried at 80° C. for 12 hours. Experimental data including elemental analysis, yield, and melting point are recorded in Table III. The Shell Four-Ball weld point, Load Wear Index and wear scar diameter of two different base greases containing this solid product are listed in Table IV.

EXAMPLE 3

Zirconium-oxy-3,5-dimercapto-1,2,4-thiadiazole

An aqueous solution of 5.0 g (0.022 m) of dipotassium 3,5-dimercapto-1,2,4-thiadiazole was added with agitation at room temperature to a solution of 7.1 g (0.022 m) of $Zr(O)Cl_2.8H_2O$ in 60 ml of water. A light yellow solid was formed, isolated by means of filtration, and dried at 100° C. for 5 hours. Elemental analysis and related data are recorded in Table III. The Shell Four-Ball extreme pressure and antiwear characteristics are listed in Table IV for two different base greases containing 5% concentration of this solid product.

EXAMPLE 4

Dibutyltin-3,5-dimercapto-1,2,4-thiadiazole

A solution of 5.9 g (0.026 m) of dipotassium 3,5-dimercapto-1,2,4-thiadiazole in 50 ml of ethanol was added slowly with agitation to an ethanol solution of 7.89 g (0.026 m) of dibutyltindichloride. The resulting reaction mixture was refluxed for 2 hours. A light yellow solid was isolated following several washes with ethanol and drying at 100° C. for 5 hours. Elemental analysis and other data of the product are recorded in Table III. The extreme pressure and antiwear characteristics of two base greases containing 5% of the solid product are listed in Table IV.

TABLE III

| Experimental Data on Zinc, Zirconyl, and Dibutyltin Dimercaptothiadiazoles | | | |
|---|---|---|---|
| Composition | Elemental Analysis | Yield | M.P., °C. |
| 1. $Zn(1,2,4-C_2N_2S_3)H_2O$ | Found: Zn, 28.1; C, 10.7; N, 12.5; S, 40.6 Calc.: Zn, 28.2; C, 10.4; N, 12.1; S, 41.5 | 92% | 320 (d) |
| 2. $Zr(O)(1,2,4-C_2N_2S_3)4H_2O$ | Found: C, 7.17; N, 8.51; S, 28.2 Calc.: C, 6.45; N, 7.52; S, 25.8 | — | 210 (d) |
| 3. $SnBu_2(1,2,4-C_2N_2S_3)$ | Found: C, 31.2; H, 4.25; N, 7.40; S, 25.0 Calc.: C, 31.5; H, 4.73; N, 7.35; S, 25.2 | 70% | 240 |

TABLE IV

| | Shell Four Ball Extreme Pressure and Antiwear Characteristics of Grease Containing Additives | | | | | |
|---|---|---|---|---|---|---|
| | Lithium-12OH Grease | | | Aluminum Complex Grease[2] | | |
| Additive, 5% | Weld Point, kg[3] | LWI[3] | Scar Dia.[4] mm | Weld Point[3] | LWI[3] | Scar Dia.[4] mm |
| 0 | 140 | 18.3 | 0.70 | 126 | 12.0 | 0.65 |
| $Zn(1,2,4-C_2N_2S_3)H_2O$ | 400 | 50.9 | 0.47 | 250 | 39.0 | 0.73 |

TABLE IV-continued

Shell Four Ball Extreme Pressure and Antiwear Characteristics of Grease Containing Additives

| Additive, 5% | Lithium-12OH Grease | | | Aluminum Complex Grease[2] | | |
|---|---|---|---|---|---|---|
| | Weld Point, kg[3] | LWI[3] | Scar Dia.[4] mm | Weld Point[3] | LWI[3] | Scar Dia.[4] mm |
| $Zr(O)(1,2,4-C_2N_2S_3)$ | 315 | 57.0 | 0.66 | 250 | 49.1 | 0.72 |
| $SnBu_2(1,2,4-C_2N_2S_3)$ | 400 | 41.0 | 0.58 | 315 | 36.9 | 0.87 |

[1] Mineral oil thickened with Lithium 12-OH stearate
[2] Mineral oil thickened with aluminum complex soap
[3] ASTM D 2596 - AISI-52100 steel balls
[4] ASTM D 2266 - AISI-52100; 1200 rpm, 40 kg, 167° F. for one hour

EXAMPLE-5

Preparation of Nickel-(II)(3,5-dimercapto 1,2,4-thiadiazole)

A solution of 5.37 g (0.0237 m) dipotassium 3,5-dimercapto-1,2,4-thiadiazole in 10 ml distilled water was added slowly with agitation to a solution of 6.24 g (0.0237 m) of Nickel(II) sulfate ($NiSO_4.6H_2O$ in 50 ml distilled water). The resulting green solution was refluxed for 2.5 hours and a black solid was deposited. The solid was isolated by filtration and was washed with distilled water and acetone, respectively. The black solid product was dried at 100° C. for several hours with a yield of 92% (m.p. 310° C. (d)). The Shell four-ball weld point of a lithium grease containing 5% of this solid is recorded in Table V, infra.

EXAMPLE-6

Preparation of Cobalt(II)3,5-dimercapto 1,2,4-thiadiazole

An aqueous solution of 5.37 g (0.0237 m) of dipotassium 3,5-dimercapto-1,2,4-thiadiazole was added slowly to a solution of 6.66 g (0.0237 m) of cobalt sulfate in water. A black precipitate immediately formed. The solid was isolated by means of filtration and washed with distilled water and acetone, respectively. After drying at 100° C. for eight hrs, a dark brown solid was obtained (84% yield, decomp. 310° C.). The Shell four-ball weld point of a lithium grease containing 5% of this solid is recorded in Table V, infra.

EXAMPLE-7

Preparation of Molybdenyl 3,5-dimercapto-1,2,4-thiadiazole

A solution of 5.37 g (0.0237 m) of dipotassium 3,5-dimercapto-1,2,4-thiadiazole in water was added to an aqueous solution of 4.70 g (0.0237 m) of molybdenum dichloride dioxide ($MoO_2Cl_2$). After the reaction mixture was refluxed for 2.5 hours, a green solid was isolated by filtration. The solid product (68% yield; decomp. 203° C.) was dried at 100° C. for about 24 hours. The Shell four-ball weld of a lithium grease containing 1% of the solid is listed in Table V, infra. Platinum, palladium, and gold compounds of the 3,5 dimercapto-1,2,4-thiadiazole can be similarly prepared and should give similar test results.

Calculated for $C_2N_2O_2S_3Mo$: C, 8.78%; N, 10.1%; S, 34.8%, Found: C, 9.43%; N, 10.9%; S, 38.1%.

TABLE 5

Shell Four-Ball Weld Points of Lithium Grease Containing Various Additives

| COMPOSITION | Weld Point |
|---|---|
| Li Grease (LG) | 140 |
| LG + 5% Ni $(1,2,4-C_2N_2S_3)$ | 250 |
| LG + 5% CO $(1,2,4-C_2N_2S_3)$ | 315 |
| LG + 1% $MoO_2(1,2,4-C_2N_2S_3)$[1] | 400 |
| LG + 5% $MoO_2(1,2,4-C_2N_2S_3)$ | >620 |

[1] The wear scar diameter is 0.55 mm vs. 0.80 mm for the base grease (40 kg, 1200 rpm and 167° F. for 1 hour).

What is claimed:

1. A lubricating composition comprising from about 80 to about 99.9 parts of a lubricant selected from the group consisting of a lithium grease, a clay grease, a silicone grease, an aluminum complex grease, a mineral oil of lubricating viscosity, and a synthetic fluid of lubricating viscosity and from about 0.1 to about 20 parts of a composition having the formula $$\begin{array}{c} N \longrightarrow C-S-R \\ \parallel \quad\quad \parallel \\ R-S-C \quad\quad N \\ \diagdown \;\; \diagup \\ S \end{array}$$

wherein R is a metallic ion.

2. The composition of claim 1 wherein the amount of the composition of said formula is 3 to 5 parts.

3. The lubricating composition of claim 1 wherein the lubricant is silicone fluid of lubricating viscosity.

4. The composition of claim 1 wherein R is selected from copper, zinc, tin, cobalt, nickel, molybdenum, silver, gold, platinum, and palladium.

* * * * *